(12) United States Patent
Karlsson

(10) Patent No.: US 8,702,660 B2
(45) Date of Patent: Apr. 22, 2014

(54) MEDICAMENT DELIVERY DEVICE

(75) Inventor: Martin Karlsson, Göteborg (SE)

(73) Assignee: SHL Group AB, Nacka Strand (SE)

( * ) Notice: Subject to any disclaimer, the term of this patent is extended or adjusted under 35 U.S.C. 154(b) by 131 days.

(21) Appl. No.: 13/062,511

(22) PCT Filed: Sep. 7, 2009

(86) PCT No.: PCT/EP2009/061565
§ 371 (c)(1),
(2), (4) Date: May 23, 2011

(87) PCT Pub. No.: WO2010/029043
PCT Pub. Date: Mar. 18, 2010

(65) Prior Publication Data
US 2011/0224622 A1  Sep. 15, 2011

(30) Foreign Application Priority Data
Sep. 9, 2008  (SE) .................................... 0801936

(51) Int. Cl.
*A61M 5/315* (2006.01)
(52) U.S. Cl.
USPC ............ 604/211; 604/210; 604/218; 604/224
(58) Field of Classification Search
USPC ........... 604/89, 207–211, 218, 223, 224, 506; 128/203.12
See application file for complete search history.

(56) References Cited

U.S. PATENT DOCUMENTS

| 5,514,097 A * | 5/1996 | Knauer ...................... 604/136 |
| 6,277,099 B1 * | 8/2001 | Strowe et al. ............... 604/207 |
| 8,152,766 B2 | 4/2012 | Karlsson et al. |
| 2006/0153693 A1 * | 7/2006 | Fiechter et al. ............. 417/63 |

FOREIGN PATENT DOCUMENTS

| EP | 0937471 A2 | 8/1999 |
| EP | 1728529 A1 | 12/2006 |
| WO | 2008/020023 A1 | 2/2008 |

OTHER PUBLICATIONS

EPO, Int'l Search Report in PCT/EP2009/061565, Dec. 17, 2009.
EPO, Written Opinion in PCT/EP2009/061565, Dec. 17, 2009.

* cited by examiner

*Primary Examiner* — Bhisma Mehta
*Assistant Examiner* — Matthew A Engel
(74) *Attorney, Agent, or Firm* — Piedmont Intellectual Property

(57) ABSTRACT

A device for delivering medicament includes a guide nut with guide ledges which cooperate with longitudinal grooves of a plunger rod for providing a rotational lock but allowing longitudinal movement of the plunger rod in relation to the guide nut that is rotationally locked to a distal housing part by engagement devices when the distal housing part and a proximal housing part are connected to each other. The device further includes a pressure release mechanism that includes slanting wedge-like surfaces arranged on the drive nut and slanting wedge-like surfaces arranged on a fixed inner annular surface of the distal housing part, which slanting wedge-like surfaces abut each other such that they move out of contact near the end of delivery of a predetermined quantity of medicament when the drive nut is rotated.

9 Claims, 2 Drawing Sheets

MEDICAMENT DELIVERY DEVICE

This application is a §371 national application of PCT/EP2009/061565 filed Sep. 7, 2009, which claims the benefit of Foreign Application No. 0801936-6 filed in Sweden on Sep. 9, 2008.

TECHNICAL AREA

The present invention relates to a medicament delivery device having a pressure relief mechanism and capable of allowing the return of a plunger rod when a new medicament container is to be used.

TECHNICAL BACKGROUND

There are numerous devices for delivering medicament on the market and also patented where the medicament is arranged in a container, such as a syringe, cartridge and the like, and wherein the medicament is exposed to pressure when it is to be delivered. A very common design is a generally tubular compartment having a stopper in one end of the compartment and a delivery member attached to the opposite end of the compartment, such as e.g. a needle, a nozzle or the like member capable of delivering medicament to a patient.

In order to deliver a quantity of medicament, the stopper is exposed to pressure, i.e. pushed into the compartment by a plunger rod, which could be done manually by a finger, which is the case for simple handheld syringes, or by pressure means such as springs, which is common in automatic or semi-automatic injectors.

In many instances it is desirable to be able to deliver a certain specified quantity of the medicament. This is for example the case with a multi-dose injection device, which is capable of delivering a number of specified, set, doses until the compartment is empty. One example is disclosed in the European patent application No. 05104734.8 where specific doses can be set before injection. The injection device disclosed is arranged with spring means for exerting a pressure on the medicament for delivering a specific dose, i.e. pushing the plunger rod and thus the stopper into the container.

The delivery of a dose requires a certain force from the spring means in order to overcome the friction between the somewhat resilient stopper and the inner surface of the cartridge and also to be able to press the medicament in liquid form through a rather small passage in the delivery member, possibly within a predetermined time.

Due to the elasticity of the components under pressure such as the stopper and also the medicament if non-newtonian, there is a prevailing pressure even when the stopper has been moved a predetermined distance and the dose has been delivered. This is in particular pronounced when handling medicament with rather high viscosity, medicament having resilient properties.

With this type of substance with high viscosity, and because very small passages of the delivery member often are used, a rather large force is required and because of the elasticity of the components, often a certain small quantity of the substance comes out of the delivery member even after performed delivery when the pressure is relieved, i.e. there is some dripping from the delivery member, which is unwanted, in particular when treating a patient and the substance may be dripping on the patient's skin, possibly causing irritation or inconvenient, undesirable effects. One solution is disclosed in WO 2008/020023 A1.

The above mentioned gel-based substances are typically injected manually, i.e. a normal type of syringe is used. Because of the rather large forces required for injecting the substances, and also due to the many small injections needed for a treatment, it is tiresome for the operator to use such a syringe during a treatment.

The plunger rods of many medicament delivery devices are threaded and cooperate with threaded nuts whereby either the plunger rod is rotated or the nut is rotated when advancing the plunger rod. For disposable medicament delivery devices this solution works very well because when the plunger rod has moved to its most forward position, the medicament container is empty and the medicament delivery device can be discarded. However, for reusable medicament delivery devices which use an auto-mechanism for delivering a dose of medicament, there is a problem when using threaded plunger rods because they have to be threaded back to their original position. One example is disclosed in EP 0937471 A1 showing a pen injector where a threaded plunger rod is threaded back to its original position. However, said pen injector does not use an auto-mechanism for delivering a dose of medicament This operation is not appreciated by most users, and may also lead to wrong handling of the device in that there could be an uncertainty as to how far the plunger rod should be threaded back. Further, there are a number of medicament delivery devices where the delivery mechanisms, and mechanisms associated with the delivery, do not permit a return of the plunger rod.

There are thus a number of aspects that are addressed with the present invention.

BRIEF DESCRIPTION OF THE INVENTION

The aim of the present invention is to minimise the unwanted expelling of excess medicament after an injection.

This aim is obtained according to the present invention by the features of the independent patent claim.

Preferable embodiments of the present invention form the subject of the dependent patent claims.

According to a major aspect of the invention, it is characterised by a device for delivering medicament, comprising a generally elongated tubular housing having opposite distal and proximal ends, said tubular housing comprising a distal housing part and a proximal housing part releasebly connected to each other by first engagement means; a container inside said proximal housing part and arranged to contain medicament; a threaded plunger rod; a drive nut threadedly connected to the threaded plunger rod; a drive member having a tensioning wheel accessible outside the distal end of the distal housing part, said drive member being connected to the drive nut via a plunger housing arranged between said drive member and said drive nut, wherein said plunger housing and said drive member are interconnected by second engagement means for providing a rotational lock of the drive member in an opposite direction when said drive member is rotated, wherein said plunger housing and said drive nut are interconnected by third engagement means for providing a rotational lock but allowing a longitudinal movement of the drive nut in relation to the plunger housing; spring force means having a first end connected to the drive member and a second end connected to a fixed point on the distal housing part such that said spring force means is tensioned when said tensioning wheel and said drive member are rotated; a manually operated activation means releasable interconnected to said plunger housing by fourth engagement means for providing a rotational locking of the plunger housing in any direction when said drive member is rotated and said spring force means is tensioned, and for releasing said rotational locking when said fourth engagement are moved away from each other, such that said drive member, said plunger housing and said drive nut are rotated in the opposite direction forcing the plunger rod to move axially exerting pressure on the medicament inside the container for expelling a certain predetermined quantity of the medicament through a delivery member; wherein the device further comprises a guide nut arranged with guide ledges which cooperate with longitudinal grooves of the plunger for providing a rotational lock but allowing a longitudinal movement of the plunger rod in relation to the guide nut, and wherein said guide nut is rotationally locked to the distal housing part by fifth engagement means when the two housing parts are connected to each other; and pressure release means comprising slanting wedge-like surfaces arranged on said drive means and slanting wedge-like surfaces arranged on a fixed inner annular surface of the distal housing part, which slanting wedge-like surfaces are abutting each other such that they move out of contact near the end of the delivery of the predetermined quantity when the drive nut is rotated.

According to one aspect of the invention, it is characterised in that said fifth engagement means are releasable arranged such that the guide nut is released from the distal housing part when the two housing parts are disconnected such that return of said plunger rod to its original position is allowed.

According to another aspect of the invention, it is characterised in that said spring force means is a torsion spring.

According to a further aspect of the invention, it is characterised in that said drive member comprises a stop ledge for limiting its movement.

There are a number of advantages with the present invention. Because the device is arranged with pressure release means, the risk of drooling or expelling excessive amounts of medicament is greatly reduced, and the use of cooperating slanting wedge-like surfaces, provides a robust mechanism without the need of many components and a distinct position where the pressure release occurs when the cooperating surfaces move out of contact. The magnitude of the pressure release may be adjusted by the height or inclination of the wedge-like surfaces.

The release of the fifth engagement means when the two housing parts are disconnected enable the plunger rod to be returned to its original position, which is an advantage for re-usable injection devices. It is then easy and simple for a patient or user to remove an empty medicament container e.g. by disconnecting the two housing halves and put a new full medicament container in the device whereby the plunger rod easily can be returned to its original position.

In order to provide the proper function, the length of the wedge-like surfaces corresponds to the movement of the plunger rod for expelling the predetermined amount of medicament.

Preferably the spring drive means is a torsion spring capable of providing a rotational movement on a component when released. It further provides the possibility of tensioning the spring by rotational movement of e.g. a tensioning wheel. In order not to rotate or tension the spring excessively, a stop ledge is provided, which limits the rotational movement.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
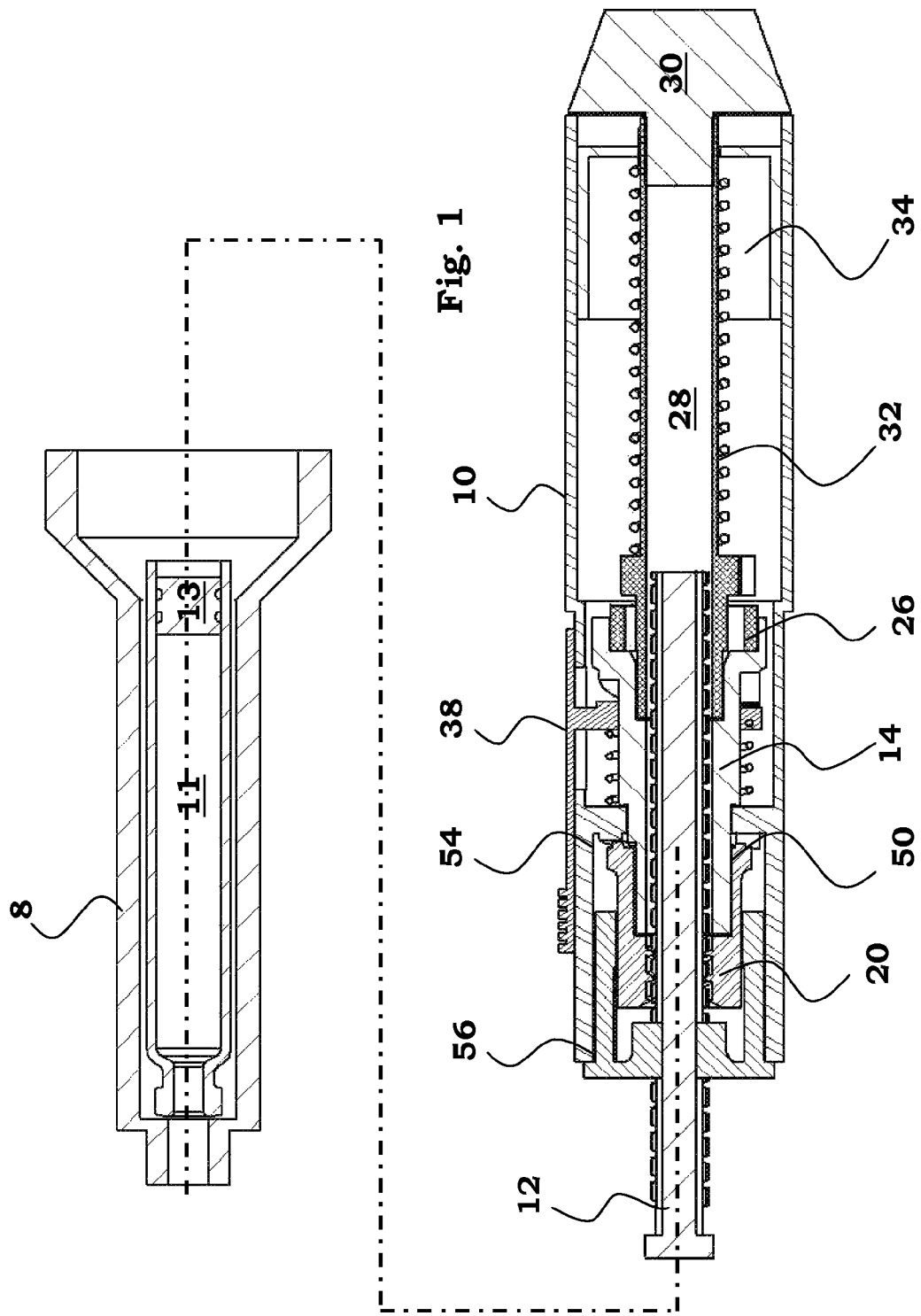
FIG. 1 is a cross-sectional view of a device according to the present invention.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

The device for delivering medicament according to the invention comprises:
  a generally elongated tubular housing having opposite distal and proximal ends, said tubular housing comprising a distal housing part 10 and a proximal housing part 8 releasebly connected to each other by first engagement means;
  a container 11 inside said proximal housing part and arranged to contain medicament;
  a threaded plunger rod 12;
  a drive nut 20 threadedly connected to the threaded plunger rod 12;
  a drive member 28 having a tensioning wheel 30 accessible outside the distal end of the distal housing part, said drive member being connected to the drive nut via a plunger housing 14 arranged between said drive member and said drive nut, wherein said plunger housing and said drive member are interconnected by second engagement means 24, 26 for providing a rotational lock of the drive member in an opposite direction when said drive member is rotated, wherein said plunger housing and said drive nut are interconnected by third engagement means 16, 18 for providing a rotational lock but allowing a longitudinal movement of the drive nut in relation to the plunger housing;
  spring force means 32 having a first end connected to the drive member and a second end connected to a fixed point on the distal housing part such that said spring force means is tensioned when said tensioning wheel and said drive member are rotated;
  a manually operated activation means 38 releasable interconnected to said plunger housing by fourth engagement means 42, 40 for providing a rotational locking of the plunger housing in any direction when said drive member is rotated and said spring force means is tensioned, and for releasing said rotational locking when said fourth engagement are moved away from each other, such that said drive member, said plunger housing and said drive nut are rotated in the opposite direction forcing the plunger rod to move axially exerting pressure on the medicament inside the container for expelling a certain predetermined quantity of the medicament through a delivery member; wherein the device further comprises:
  a guide nut 56 arranged with guide ledges 58 which cooperate with longitudinal grooves 60 of the plunger for providing a rotational lock but allowing a longitudinal movement of the plunger rod in relation to the guide nut, and wherein said guide nut is rotationally locked to the distal housing part by fifth engagement means when the two housing parts are connected to each other; and pressure release means comprising slanting wedge-like surfaces 50 arranged on said drive means 20 and slanting wedge-like surfaces 54 arranged on a fixed inner annular surface 52 of the distal housing part, which slanting wedge-like surfaces 50, 54 are abutting each other such that they move out of contact near the end of the delivery of the predetermined quantity when the drive nut is rotated.

As seen in FIG. 1, the proximal housing part 8 is arranged as a medicament container holder 8, wherein the medicament container 11 is arranged. The plunger rod 12 is arranged to act on a stopper 13 inside said medicament container for expelling a dose of medicament through the delivery member upon activation. The delivery member being a part of the medicament container as e.g. a needle when the medicament container is a syringe or as a releasable delivery member e.g. a pen needle, that is attached to the proximal end of the proximal housing part.

The plunger rod 12 is coaxially arranged inside the plunger housing 14 which has a generally tubular shape. One end part of the plunger housing is arranged with the third engagement means as e.g. spline grooves 16 on its outer surface, FIG. 2. The spline grooves mate with corresponding third engagement means as e.g. spline ridges 18 on an inner surface of the drive nut 20, FIG. 2. Further, the plunger housing 14 is arranged with a ring-shaped part 22, where the inner surface of the ring is arranged with the second engagement means as e.g. transversal stop ledges 24, FIG. 2. These stop ledges cooperate with the corresponding second engagements means as e.g. flexible arms 26 of the drive member 28, FIG. 2. The distal end of the drive member 28 protrudes through the distal end of the housing, where the tensioning wheel 30 is fixedly attached, for rotating said drive member.

However the stop ledges 24 and flexible arms are arranged such that the drive member 28 may only be rotated in one direction in relation to the plunger housing, where the flexible arms 26 slide over the stop ledges 24. In the other direction, the ends of the flexible arms 26 abut the stop ledges 24, thereby blocking the rotation, FIG. 2. The spring force means as e.g. a torsion spring 32 is coaxially arranged around the drive member 28 and have a first end connected to the drive member and a second end connected to a fixed point on the distal housing part. In the example shown in the figures, the fixed point is a tubular part 34 which is fixedly connected to distal housing part or is integrated with the distal housing part during the manufacturing process. The drive member is further arranged with a stop ledge 36 co-acting with a corresponding stop ledge attached to the distal housing part, (not shown) for limiting the rotation of the drive member, FIG. 2.

Figure 2:
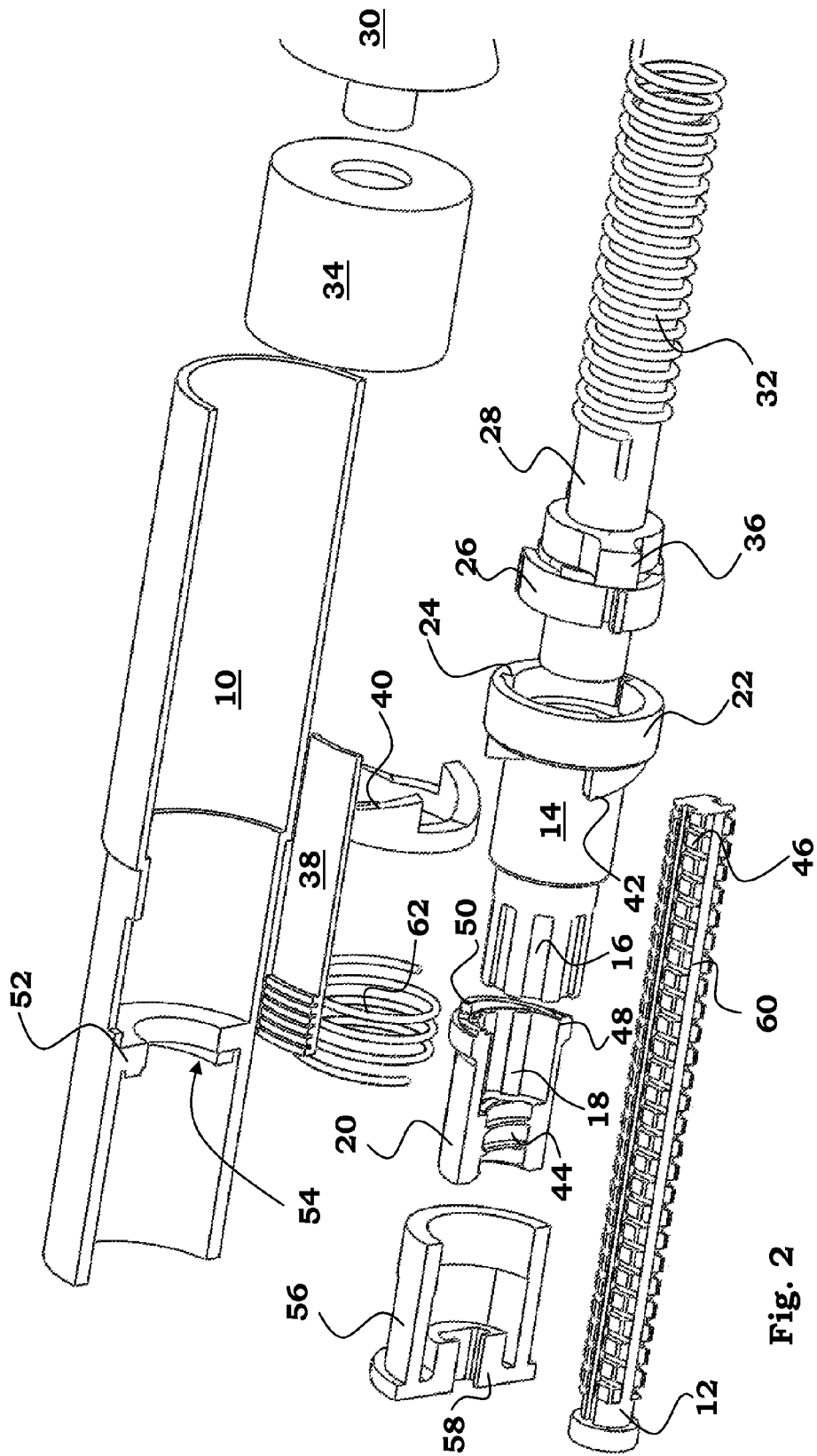
FIG. 2 is an exploded view of the device of FIG. 1.

Further, the manually operated activation means as e.g. an activation button 38 comprises a ring shaped part having the fourth engagement means as e.g. wedge-shaped stop ledges 40 cooperating with corresponding fourth engagement means as e.g. stop ledges 42 on the plunger housing 14, FIG. 2. The activation button further comprises a transversal part protruding through a through hole on the longitudinal surface of the distal housing part, and a longitudinally extending outer part connected to the transversal part. Further, a return spring 62 is arranged between the ring shaped part of the activation button and an annular ledge surface on the inner surface of the distal housing part, such that the return spring forces the wedge-shaped stop ledges 40 to be in contact with the stop ledges 42 on the plunger housing 14.

The inner surface of the drive nut 20 is further provided with threads 44 which cooperate with threads 46 on the outer surface of the plunger rod 12. The drive nut 20 is further arranged with an annular ledge 48 having a number of slanting wedge-shaped surfaces 50 around said ledge, the function of which will be described below. The fixed inner annular surface of the distal housing part comprises the corresponding slanting wedge-shaped surfaces 54, the function of which will be described below.

The plunger rod 12 is further arranged through the guide nut 56 which is rotationally locked to the distal housing part by the fifth engagement means as e.g. corresponding splines or the like, both on the guide nut and on the proximal end of the distal housing part when the proximal housing part is connected to the distal housing part. Said fifth engagement means are releasable arranged such that the guide nut is released from the distal housing part when the two housing parts are disconnected such that return of said plunger rod to its original position is allowed.

The device is intended to function as follows. A medicament container 11 is placed in the proximal housing part 8, which then is engaged to the distal housing part, whereby the guide nut 56 becomes rotationally locked.

When a dose is to be delivered the tensioning wheel 30 is rotated, whereby the drive member 28 also is rotated. This rotation causes the torsion spring 32 to be tensioned. During rotation, the flexible arms 26 move out of contact with the stop ledges 24 of the ring-shaped member 22 of the plunger housing 14 until they are moved in contact with subsequent stop ledges 24. The drive member 28 is prevented from being rotated back because of the contact of the flexible arms 26 with the stop ledges 24.

Further, the plunger housing is in turn prevented from rotating because of the wedge-shaped stop ledges 40 of the activation button are in contact with the stop ledges 42 on the plunger housing 14. The tensioning wheel 30 is rotated until the stop ledge 36 comes in contact with the corresponding stop ledge. This ensures that the user cannot turn the tensioning wheel beyond a preset position, and thus that a too large dos cannot be set. In the embodiment shown, the tensioning wheel can be turned 120 degrees for setting a dose. Because of this the flexible arms 26 together with the stop ledges 24 are three and have a pitch of 120 degrees. The pitch of 120 degrees is also used for the wedge-shaped components 50 of the drive nut 20 as well as the wedge-shaped components 54 of the housing. It is to be understood that pitches other than 120 degrees can be used, depending on the dose size and/or the design of other components such as the pitch of the threads of the plunger rod and drive nut.

The user now positions the medicament delivery device at the delivery site and manually activates the medicament delivery device by sliding the activation button 38 against the force of the return spring 62. This causes the stop ledges 40 of the activation button to move out of contact with the stop ledges 42 of the plunger housing. The drive member 28 is now free to rotate by the force of the spring 32, and because of the connection between the flexible arms 26 and the stop ledges 24, the plunger housing 14 also rotates, and due to the splines connection between the plunger housing 14 and the drive nut 20, the latter is also rotated.

Because of the rotation of the drive nut 20, which is in threaded engagement with the threads 46 of the plunger rod 12, and because of the rotational lock of the plunger rod with the guide nut 56, the plunger rod is axially advanced, which causes it to move the stopper and to expel a dose of medicament. During the rotation of the drive nut 20, the slanting, wedge-like surfaces 50 of the drive nut 20 will slide on the corresponding wedge-like surfaces 54 of the distal housing part 10, which causes the drive nut 20 to move axially in the proximal direction, to the left in the drawings, which is allowed by the splines connection with the drive member 28.

The wedge-like surfaces 50, 54 of the drive nut and the housing are designed such that there is an abrupt ending of the wedge-shape just before the end-of-dose movement. The abrupt ending causes the drive nut 20 to move somewhat in the opposite direction, i.e. the distal direction, whereby the plunger rod 12 also is moved in that direction. This movement of the plunger rod effectively releases the pressure that the plunger rod is exerting on the stopper and thus on the medicament in the container. Because of the removal of the pressure, drooling after performed delivery is to a large extent avoided. In order to increase the abrupt ending motion, a spring (not shown) can be arranged between the drive nut and the guide nut, capable of urging the drive nut towards the distal end of the device and thus towards the annular ledge 52.

The delivery device can now be removed from the delivery site. For subsequent delivery, where a multi-dose container is used, a fresh delivery member is attached, if used, and the tensioning wheel is rotated to set the dose and tension the spring. When the multi-dose container is empty, or if a single-dose container is used, the proximal housing part is detached from the distal housing part and the medicament container is removed. The now proximally advanced plunger rod may be moved back in its original position, which is allowed since the guide nut now is free to rotate, whereby the plunger rod also can be rotated. A new container is placed in the proximal housing part, after which the latter is again connected to the distal housing part.

It is to be understood that the embodiment described above and shown in the drawings is to be regarded only as a non-limiting example of the present invention and that it may be modified in many ways within the scope of the patent claims.

The invention claimed is:

1. A device for delivering medicament, comprising:
   a generally elongated tubular housing having opposite distal and proximal ends, the tubular housing comprising a distal housing part and a proximal housing part releasably connected to each other by a first engagement mechanism;
   a container inside the proximal housing part and arranged to contain a medicament;
   a threaded plunger rod;
   a drive nut threadedly connected to the threaded plunger rod;
   a drive member having a tensioning wheel accessible outside the distal end of the distal housing part, wherein the drive member is connected to the drive nut via a plunger housing arranged between the drive member and the drive nut, the plunger housing and the drive member are interconnected by a second engagement mechanism configured for rotationally locking the drive member in an opposite direction when the drive member is rotated, and the plunger housing and the drive nut are interconnected by a third engagement mechanism configured for rotationally lock but allowing longitudinal movement of the drive nut in relation to the plunger housing;
   a spring force mechanism having a first end connected to the drive member and a second end connected to a fixed point on the distal housing part such that the spring force mechanism is tensioned when the tensioning wheel and the drive member are rotated;
   a manually operated activation mechanism releasably interconnected to the plunger housing by fourth engagement devices configured for rotationally locking the plunger housing in any direction when the drive member is rotated and the spring force mechanism is tensioned, and for releasing rotational locking when the fourth engagement devices are moved away from each other, such that the drive member, the plunger housing, and the drive nut are rotated in the opposite direction, forcing the plunger rod to move axially, exerting pressure on the medicament inside the container for expelling a predetermined quantity of the medicament through a delivery member;
   a guide nut arranged with guide ledges that cooperate with longitudinal grooves of the plunger for rotationally locking but allowing longitudinal movement of the plunger rod in relation to the guide nut, wherein the guide nut is rotationally locked to the distal housing part; and
   a pressure release mechanism, comprising slanting wedge-like surfaces arranged on the drive nut and slanting wedge-like surfaces arranged on a fixed inner annular surface of the distal housing part, wherein the slanting wedge-like surfaces abut each other such that they move out of contact near an end of delivery of the predetermined quantity when the drive nut is rotated.

2. The device of claim 1, wherein the drive member comprises a stop ledge for limiting its movement.

3. The device of claim 1, wherein the spring force mechanism includes a torsion spring.

4. The device of claims 3, wherein the drive member comprises a stop ledge for limiting its movement.

5. The device of claim 1, wherein the guide nut is released from the distal housing part when the housing parts are disconnected such that return of the plunger rod to its original position is enabled.

6. The device of claim 5, wherein the drive member comprises a stop ledge for limiting its movement.

7. The device of claim 5, wherein the spring force mechanism includes a torsion spring.

8. The device of claim 7, wherein the drive member comprises a stop ledge for limiting its movement.

9. The device of claim 1, wherein the slanting wedge-like surfaces move out of contact near an end of delivery of the predetermined quantity when the drive nut is rotated, causing the drive nut to move in a distal direction, whereby the plunger rod also is moved in that direction.

* * * * *